WILLIAM A. LIGHTHALL.

Improvement in Steam-Enginery for Surface Condensers.

No. 4,894. Reissued May 7, 1872.

*Witnesses:*

Wm. Reddy

A. Livingston Mills

*Inventor:*

William A. Lighthall

By J. P. Stuck

AM. PHOTO-LITHOGRAPHIC CO. N.Y. (OSBORNE'S PROCESS.)

UNITED STATES PATENT OFFICE.

WILLIAM A. LIGHTHALL, OF NEW YORK, N. Y.

IMPROVEMENT IN STEAM-ENGINERY FOR SURFACE-CONDENSERS.

Specification forming part of Letters Patent No. 89,156, dated April 20, 1869; reissue No. 4,894, dated May 7, 1872.

*To all whom it may concern:*

Be it known that I, WILLIAM A. LIGHTHALL, of the city, county, and State of New York, have invented certain new and useful Improvements Relating to Surface-Condensers for Steam-Engines; and I do hereby declare that the following is a full and perfect description of the same, reference being had to the accompanying drawing and to the letters of reference marked thereon, in which—

Figure 1:
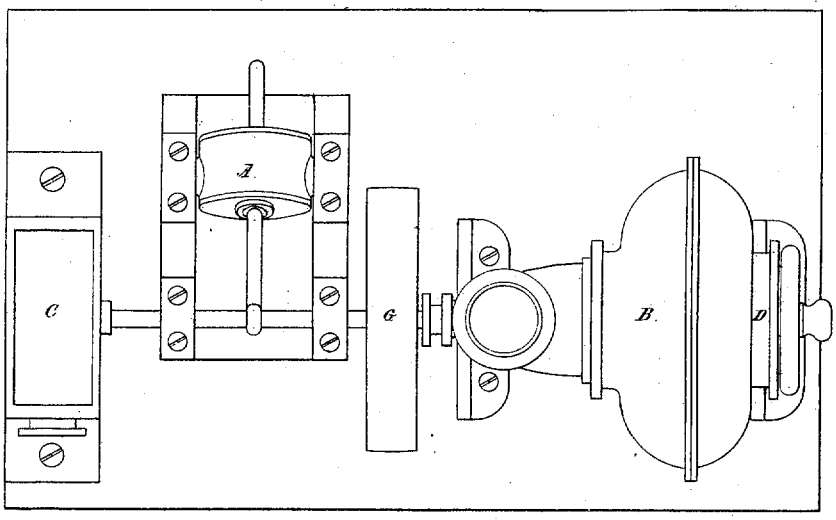
Figure 2:
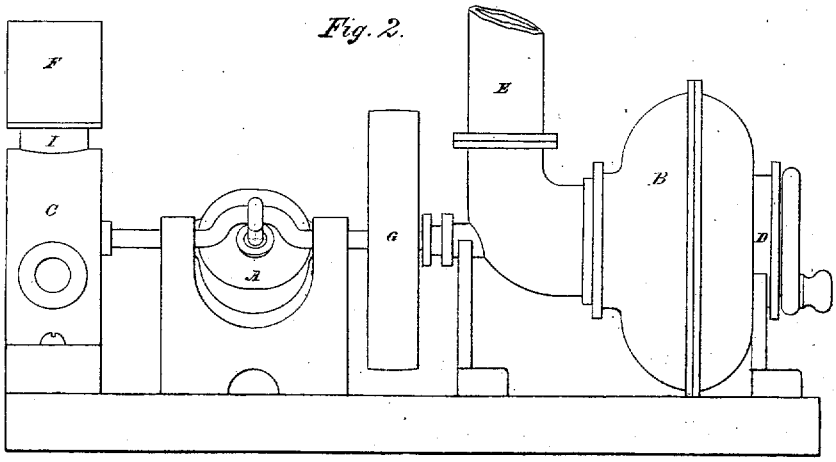

Figure 1 is a plan view, and Fig. 2 is a side elevation.

I find in practice that the rotary circulating-pump, when used to furnish cooling-water to the surface-condenser of a steam-engine, should be independent of the movement of the main propelling-engine, to which the surface-condenser is attached, so that it can operate when such engine is not in motion. I also find, in practice, that the rotary air-pump, in this combination, possesses important advantages over all forms of the reciprocating air-pump, some of which are, the steadiness of flow of the water, economy of space, power, steam in operating it, weight, and cost of keeping it in repair, the small liability to get out of order, and the little expense attending the increasing of its capacity, when such increase is desired. The securing these advantages is the principal purpose of my combination, embracing the said rotary air-pump with the rotary supply-pump and independent driving-engine. The independent driving-engine operates both the rotary circulating-pump to furnish cooling-water to the surface-condenser, and also the rotary "air-pump," to take from the condenser the water and incondensible gases in the surface-condenser. This combination is, therefore, nearly automatic in its operation, as the greater the pressure of steam, so is relatively, the greater number of revolutions of the rotary pump for the supply of cooling-water, and of the rotary air-pump for removing from the condenser the water and gases.

Referring to the drawing hereto attached, A is an independent engine, which drives both the rotary circulating-pump and the rotary air-pump. It is so connected with the condenser that it is almost entirely operated by reason of the vacuum in the condenser, causing thereby the use of much less "live steam" to operate it than that heretofore necessary. B is the rotary circulating-pump, to furnish the supply of cooling-water to the surface-condenser through the proper pipes and attachments. C is the rotary "air-pump," which is attached to and driven by the shaft of the engine A to effect its purpose named.

The surface-condenser to which I intend to attach this arrangement is not shown in the drawing, but it will be apparent that the combination and arrangement will fully answer for any condenser of the surface class now made and used. In this combination I limit myself to the use of the circulating-pump B and the rotary air-pump C, represented in the drawing, when the same are operated by an independent engine or other motor.

I know that the combination of the reciprocating circulating-pump and reciprocating air-pump has been heretofore used, driven together by the main propelling engine. I therefore disclaim such arrangement, and only claim the combination of the rotary circulating-pump B, and the rotary air-pump C, when driven by the independent engine A, the benefit of which will be apparent to practical engineers.

What I claim as my invention, and desire to secure by Letters Patent, is—

The combination of the driving-engine A, rotary circulating-pump B, and rotary air-pump C, when all co-operate together to perform the functions herein set forth, substantially as described.

WM. A. LIGHTHALL.

Witnesses:
A. LIVINGSTON MILLS,
J. H. MINSON.